United States Patent [19]

Bundy

[11] 4,151,176

[45] Apr. 24, 1979

[54] BIOPRECURSORS OF 9-DEOXY-6,9α-NITRILO-PGF₁

[75] Inventor: Gordon L. Bundy, Portage, Mich.

[73] Assignee: The Upjohn Company, Kalamazoo, Mich.

[21] Appl. No.: 910,412

[22] Filed: May 30, 1978

Related U.S. Application Data

[63] Continuation-in-part of Ser. No. 807,514, Jun. 17, 1977, Pat. No. 4,097,489.

[51] Int. Cl.² ................... C07D 209/52; A61K 31/40
[52] U.S. Cl. ............................... 260/326.27; 424/274
[58] Field of Search .................................. 260/326.27

[56] References Cited

U.S. PATENT DOCUMENTS

| | | | |
|---|---|---|---|
| 3,931,289 | 1/1976 | Bundy | 260/473 A |
| 3,983,157 | 9/1976 | Bundy | 260/473 A |
| 3,983,158 | 9/1976 | Bundy | 260/473 A |
| 4,097,489 | 6/1978 | Bundy | 260/326.27 |

FOREIGN PATENT DOCUMENTS 2535693  3/1976  Fed. Rep. of Germany ...... 260/473 A

OTHER PUBLICATIONS

Johnson et al.; Prostaglandins, vol. 12, p. 915, (1976).

Primary Examiner—Donald G. Daus
Assistant Examiner—Mary Lee
Attorney, Agent, or Firm—Robert A. Armitage

[57] ABSTRACT

The present invention relates to novel bioprecursors for prostaglandin analogs of the formula

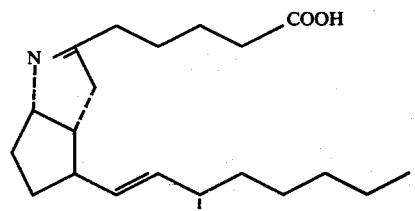

or

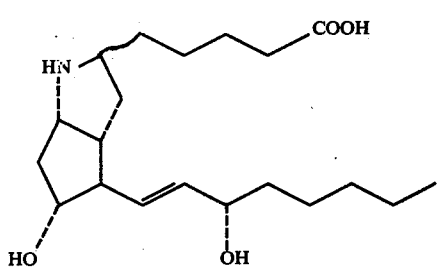

These bioprecursors are useful for the same pharmacological purposes as the corresponding prostaglandin analogs, being hydrolyzable thereto in vivo.

1 Claim, No Drawings

BIOPRECURSORS OF 9-DEOXY-6,9α-NITRILO-PGF$_1$

CROSS REFERENCE TO RELATED APPLICATIONS

The present invention is a continuation-in-part of Ser. No. 807,514, filed June 17, 1977, now U.S. Pat. No. 4,097,489.

BACKGROUND OF THE INVENTION

The present invention relates to the bioprecursors of certain novel prostaglandin analogs described below.

The disclosure of the novel prostaglandin analogs is found in parent application Ser. No. 807,514, the relevant disclosure of which is incorporated here by reference.

The prostaglandins are a series of compounds derived from unsaturated fatty acids, notably arachidonic acid. The prostaglandins are characterized by pronounced pharmacological activity and accordingly represent useful drugs or pharmacological agents.

Pharmacological agents are typically characterized by functional groups which, when they react with a wide variety of chemical reagents, produce distinctive derivatives of such pharmacological agents. Such functional groups or reactive sites include carboxyl, hydroxyl, sulfhydryl, and amine groups. Such derivatives of pharmacologically active agents are typically distinctive in both physical and pharmacological properties as compared to the underivatized agents themselves. Among the modified physical properties exhibited by such derivatives are typically aqueous solubility, lipophilicity, crystallinity, and other parameters pertinent to formulation for pharmacological purposes. Additionally, the extent and duration of the pharmacological effects exhibited by such derivatives is often highly distinctive from the effects exerted by the underivatized agent itself.

Pharmacological agents are often characterized by various undesirable physical, chemical, and biological properties. In the process of commercialization of such pharmacological agents into medicinally acceptable drugs, numerous techniques are employed to reduce these undesirable effects. For example, a biological approach in dealing with undesirable physical, chemical, and biological properties would include varying the route of administration, thereby possibly increasing absorption, elimination of GI tract irritability, and the like. Since for most substances, oral administration represents a highly preferred route, such biological approaches to the minimization of the undesirable physical, chemical, and biological properties of pharmacological agents are limited.

A second approach to the elimination of undesirable physical, chemical, and biological properties for pharmacological agents known in the art is a physical approach, i.e., modification of the dosage form in which the drug is delivered. For example, known in the art are devices which are bio-implantable or which exhibit controlled release rates of drug.

However, a further recognized and in many cases preferred means of minimizing or eliminating the undesirable physical, chemical, or biological properties of drugs is by chemical means, in particular, the transformation of these pharmacological agents to distinctive derivatives. Such derivatives of pharmacological agents are known in the art as being either reversible or irreversible derivatives. Such irreversible derivatives, commonly referred to as analogs of the initial pharmacological agent, often exhibit modified biological activity and may introduce new undesired physical, chemical, and biological properties, even where the undesirable physical, chemical and biological properties of the pharmacological agent itself are mitigated in the irreversible derivative.

Reversible derivatives of pharmacological agents are known in the art and are defined as those derivatives of pharmacological agents which upon introduction into the host animal are chemically or biochemically hydrolyzed to the pharmacological agent itself.

Moreover such chemical or biochemical hydrolysis in vivo of the derivative liberates, in addition to the underivatized agent itself, a further byproduct, as indicated by the following equation:

$$A-B \xrightarrow{H_2O} AH + BOH \qquad I$$

Thus where AH represents a pharmacologically active substance and A-B a derivative thereof, the hydrolysis in vivo of A-B yields the byproduct BOH, as well as AH.

A bioprecursor for a pharmacological agent is any reversible derivative of such a pharmacological agent which meets the following criteria:

(a) The derivative is hydrolyzable in vivo to the pharmacological agent itself and is in fact hydrolyzed in vivo to the pharmacological agent itself upon administration to an animal or patient for pharmacological purposes;

(b) The rate of hydrolysis in vivo for the derivative is relatively rapid such that the rate limiting means of disposition of the derivative in vivo is hydrolysis to the pharmacological agent itself;

(c) The derivative is either weakly pharmacologically active or pharmacologically inactive unless and until hydrolysis in vivo to the pharmacological agent itself;

(d) If the derivative exhibits substantial pharmacological activity itself, no greater untoward pharmacological effects are present upon administration to a patient or animal therewith; and (e) The byproduct obtained by hydrolysis of the derivative is essentially non-toxic at the levels being released by hydrolysis in vivo and is pharmacologically inert or substantially devoid of untoward pharmacological effects at levels released by in vivo hydrolysis.

The rationale for the preparation of bioprecursors is known. See for example, Sinkula, A. A., et al., Journal of Pharmacological Science, 58:1389 (1969), 62:1102 (1973), 62:1757 (1973), 62:1106 (1973), and 63:842 (1974). Bioprecursors have also been referred to in the art as "prodrugs". See, for example, Swintosky, J. V., et al., J. Pharm. Sci., 55:992 (1977); Caldwell, H. C., et al., J. Pharm. Sci., 56:920 (1967); Swintosky, J. V., et al., J. Pharm. Sci., 57:752 (1968); Dittert, L. W., et al., J. Pharm. Sci., 57:774 (1968); Dittert, L. W., et al., ibid, 57:780 (1968); Rattie, E. S., et al., J. Pharm. Sci., 59:1738 (1970); Takechi, H., et al., "Abstracts of Papers", APhA Academy of Pharmaceutical Sciences, Houston, Tex. meeting, April 1972, p. 64; and Stella, V., et al., ibid, p. 76. Likewise, bioprecursors have been referred to as latentiated drugs. See, for example, Harper, N. J., J. Med. Pharm. Chem., 1:467 ; (1959); Harper, N. J., Progr. Drug Res., 4:221 (1962); and Harper, N. J., in "Absorption and Distribution of Drugs", T. B. Binns, Ed., Williams & Wilkins, Baltimore, Md., 1964, p. 103. For a comprehensive review of the rationale for the design of bioprecursors, see Sinkula, A. A., et al., J. Pharm. Sci., 64:3259 (1975) and the numerous references cited therein.

Bioprecursors are prepared at any one of a number of reactive sites in a pharmacological agent. For pharmacological agents containing carboxyl groups as reactive sites, esters, amide, anhydrides, and mixed anhydrides thereof are examples of acid derivatives from which useful bioprecursors are selected. In this connection, acid derivatives are hydrolyzed as indicated in Formulas II-V, as follows:

$$R_1COOE \xrightarrow{H_2O} R_1COOH + EOH \qquad II$$

$$R_1CONR_3R_4 \xrightarrow{H_2O} R_1COOH + R_3R_4NH \qquad III$$

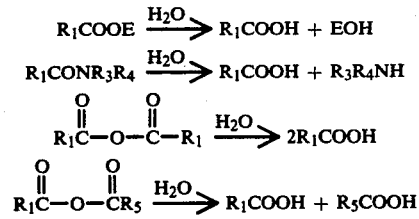

Accordingly, the selection from among carboxylic acid derivatives for suitable bioprecursors requires a careful analysis of the byproducts (e.g., alcohols, amines, and other carboxylic acids) which are liberated by hydrolysis in vivo thereof. By methods readily known in the art, the pharmacological acceptability, including the essential non-toxicity and pharmacological inertness or absence of untoward pharmacological effects, for the byproducts is readily assessed. For example, toxicological tests on standard laboratory animals will readily determine the level and extent of toxicity for the byproducts produced by in vivo hydrolysis. Likewise, the existence and extent of hydrolyzability in vivo is readily assessed by standard laboratory techniques. For example, radio-labelled reagents may be employed to prepare radio-labelled derivatives of pharmacologically active agents and the pattern of recovery of such radioactivity will determine the extent of hydrolysis (i.e., the portion of the total radioactivity recovered in the form of byproducts) as compared to the extent of disposition of derivative through excretion or catabolism. Further in this connection, a bio-assay is conjunctively employed in determining the extent of hydrolysis, by measuring the extent of pharmacological activity observed upon administration of the derivative and comparing that result with the known pharmacological activity of the pharmacologically active agent itself. The bio-assay technique is further useful in assessing which derivatives are inactive or weakly active unless and until the hydrolysis thereof yields the pharmacologically active agent.

Using the same techniques by which bioprecursors are selected from carboxylic acid derivatives, there are determined the corresponding bioprecursors for hydroxylated pharmacological agents, i.e., compounds of the formula $R_1OH$. Such derivatives include, for example, acylates, which are hydrolyzable according to the following formula:

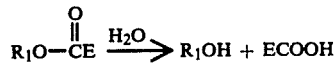

Likewise, amine-containing pharmacological agents are derivatized to corresponding acylates in the production of bioprecursors.

For compounds exhibiting multiple reactive sites, multiple derivatives, including cyclic forms, represent further entities from among which bioprecursors are selected. For example, hydroxy acids of the formula $OH-X_1-COOH$ may exhibit lactone derivatives, hydrolyzed as follows:

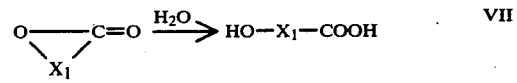

Similarly, amino acids of the formula $H_2N-X_1-COOH$ exhibit lactams which are hydrolyzable as follows:

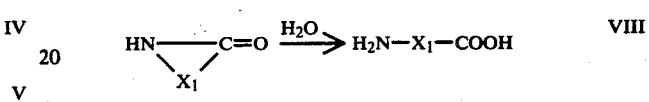

Finally, as indicated above, mixed derivatives of hydroxy acids or amino acids (e.g., acylate esters) are hydrolyzable, in accordance with Formula IX.

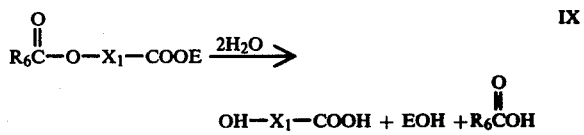

As indicated previously, bioprecursors are useful for the same pharmacological purposes as their corresponding pharmacological agent, often in the same manner, but further exhibit modified physical and pharmacological properties. Thus, in many cases, the undesirable properties of any particular pharmacological agent, which cannot be overcome by other means, are favorably affected by the preparation and use of a bioprecursor thereof. Thus, pharmacological agents designed for oral use may be rendered more palatable through employment of an appropriate bioprecursor and untoward effects, such as GI tract irritability, pain on injection, inadequate absorption, and inadequate chemical stability, may be overcome.

Examples of bioprecursors are known in the art, see, for example, the description of the bioprecursors of ampicilin described by vonDaehne, et al, J. Med. Chem., 13:607 (1970); and Antimicrobe Ag. Chemother., 1970:431. There are likewise known in the art bioprecursors for convallatoxin described by German Offenlegungsschrift No. 2,042,646; hydantoin described by Stella, V., et al., J. Pharm. Sci. 62:962 (1973); chlorphenesin described by German Offenlegungsschrift No. 2,242,781; acetamidophen described by Japanese patent No. 7,303,363; acetylsalicyclic acid described by German Offenlegungschrift No. 2,134,672 and Croft, D. N., et al., Brit. Med. J., 3:545 (1972); N-allylnoroxymorphone described by Linder, C., et al., J. Med. Chem., 16:553 (1973); nicotinic acid described by Linari, G., Arzneim-Forsch., 22:1419 (1972); 15-methylprostaglandin $F_2\alpha$ described by Magee, W. E., et al., Biochim. Biophy. Acta, 306:270 (1973); procaine described by Weiner, B.-Z., et al., J. Med. Chem., 16:573 (1973); $\alpha$-amino-p-toluenesolfonamide described by Stella, V. J., Aust. J. Pharm. Sci., NS2:57 (1973) and White, M. G., et al., N. Engl. J. Med., 284:1281 (1971);

hexachlorophene described by Techechi, H., et al., "Abstracts of Papers," APhA Academy of Pharmaceutical Sciences, Houston, Tex. meeting, Apr. 1972, p. 64; oleandomycin described by Celmer, W. D., Antibiot. Annu., 1958-1959, 277; erythromycin described by Sinkula, A. A., J. Pharm. Sci., 63:842 (1974), Stephens, V. C., et al., J. Amer. Pharm. Ass., Sci. Ed., 48:620 (1959), and Bell, S. M., Med. J. Aust., 2:1280 (1971); clindamycin described by Sinkula, A. A., et al., J. Pharm. Sci., 62:1106 (1973), Forist, A. A., et al., J. Pharmacokinet. Biopharm. 1:89 (1973), and Kauffman, R. E., et al., Clin. Pharmacol. Ther., 13:704 (1972); α-carboxybenzylpenicillin described by U.S. Pat. No. 3,681,342; α-aryl-β-aminoethyl penicillin described by U.S. Pat. No. 3,719,668; penicillin (general structure) described by Jensen, A. B. A., et al., J. Chem. Soc., 1965, 2127; α-aminobenzylpenicillin described by Hansson, E., et al., Antimicrob. Ag. Chemother., 1967, 568, and Ramsey, C. H., et al., Arzneim.-Forsch., 22:1962 (1972); 6-(D-α-sulfoaminophenylacetamido) penicillin described by U.S. Pat. No. 3,653,265; carbenicillin described by English, A. R., et al., Antimicrob. Ag. Chemother, 1:185 (1971) and Hobbs, D. C., ibid, 2:272 (1972); α-aminobenzylpenicillin described by von Daehne, W., et al., J. Med. Chem., 13:607 (1970), von Daehne, W., et al., Antimicrob. Ag. Chemother, 1970, 431, Foltz, E. L., et al., Antimicrob. Ag. Chemother, 1970, 442, Jordon, M. C., et al., ibid, 1970, 438, Hultberg, E. R., et al., Scand. J. Infect. Dis., 4:149 (1972), and by U.S. Pat. No. 3,697,507; penicillin G described by Yurchenco, J. A., et al., Chemotherapy, 17:405 (1972); penicillin V described by Yurchenco, J. A., et al., 17:405 (1972); α-aminobenzylpenicillin described by Jusko, W. J., et al., J. Pharm. Sci. 62:69 (1973) and Jusko, W. J., et al., Clin. Pharmacol. Ther., 14:90 (1973); hetacillin described by U.S. Pat. No. 3,679,633; doxycycline described by Belgian Patent No. 774,717; colistin described by Japanese Patent No. 7,211,961; tetracycline described by French Patent No. 2,126,443; 7-acylaminocephalosporins described by Japanese Patent No. 4,720,187 and Belgian Patent No. 781,659; α-amino (ur ureido) cyclohexadienylalkyl penicillins and cephalosporins described by German Offenlegungsschrift No. 2,152,745; 7-acylaminocephalosporins described by German Offenlegungsschrift No. 2,223,375; nandrolone described by van der Vies, J., Acta Endocrinol. 49:271 (1965); 9α-fluorohydrocortisone described by Winter, C. A., et al., J. Amer. Pharm. Asso., Sci. Ed., 46:515 (1957); estradiol described by Gardi, R., et al., J. Med. Chem. 16:123 (1973); oxymetholone described by Evans, D. D., et al., Steroids 5:441 (1965); methylprednisolone described by Novak, E., et al., Clin. Pharmacol. Ther., 13:148 (1972); testosterone described by Fukushima, D. K., et al., Steroids, 19 385 (1972) and Chang, E., et al., J. Med. Chem., 9:433 (1966); 19-nortestosterone described by Rapala, R. T., et al., J. Med. Chem., 8:580 (1965); 9-(β-D-arabinofuranosyl)adenine described by U.S. Pat. No. 3,651,045; cortisol, prednisolone, dexamethasone described by Melby, J. C., et al., Metabolism 10:75 (1961); prostaglandin described by U.S. Pat. No. 3,764,673; and salicyclic acid described by Dittert, L. W., et al., J. Pharm. Sci., 57:828 (1968) and Misher, A., et al., ibid., 57:1128 (1968). Also, isocyanate, R—N=C=O described by DeVita, V. T., et al., Cancer Res., 25:1876 (1965), Montgomery, et al., J. Med. Chem. 10:668 (1967), and Johnston, T. P., et al., J. Med. Chem. 10:675 (1967); testosterone described by Fels, E., J. Clin. Endocrinol., 4:121 (1967); dromostanolone described by Seay, D. G., et al., Cancer Chemother. Rep., 56:89 (1972); urea described by Fishbein, W. N., et al., Clin. Pharmacol. Ther., 5:574 (1964); normeperidine described by Kupchan, S. M., et al., J. Med. Chem., 10:960 (1967); morphone, phenazocine described by Kupchan, S. M., et al., J. Med. Chem., 10:959 (1967); diethylstilbestrol described by Harper, N. J., J. Med. Pharm. Chem., 1:467 (1959) and German Offenlegungsschrift No. 2,231,486; methotrexate, 3',5'-dichloromethotrexate described by Johns, D. J., et al., Drug Metab. Dispos., 1:580 (1973); phenethylamine, dl- and d-amphetamine, l-ephedrine, dl-p-hydroxyamphetamine described by U.S. Pat. No. 3,742,022 and Verbiscar, A. J., et al., J. Med. Chem., 13:1176 (1970); dopamine; 3,4-dihydroxyphenethylamine described by Casagrande, C., et al., Farmaco, Ed. Sci., 28:143 (1972); norepinephrine described by Creveling, C. R., et al., Experientia 25:26 (1969); cytosine arabinoside described by Gray, G. D., et al., Biochem. Pharmacol., 21:465 (1972); hydroxyurea described by Yu, R. J., et al., Proc. Amer. Ass. Cancer Res., 14:46 (1973); dichloroisocyanatophosphine oxide described by Papanastassiou, Z. B., et al., J. Med. Pharm. Chem., 5:1000 (1962); N,N-bis(2-chloroethyl)-phosphorodiamidic acid described by Friedman, O. M., Cancer Chemother. Rep., 51:327 (1967), Foley, G. E., et al., Cancer Res. 21:57 (1961), Brock, N., et al., Cancer (Philadelphia), 20:900 (1967), Colvin, M., et al., Cancer Res., 33:915 (1973), and Milner, A. N., et al., Cancer Chemother. Rep., 51:343 (1967); nitrogen mustard described by Friedman, O. M., Cancer Chemother, Rep., 51:347 (1967) and Kaplan, M. A., et al., Nature (London), 205:399 (1965); allylamine described by Tsou, K. C., et al., J. Pharm. Sci., 56:484 (1967); nitrogen mustard described at Schaeppi, U., et al., Cancer Chemother. Rep., 4, Part 3, 85 (1973), Wall, M. E., et al., J. Med. Chem., 12:810 (1969), Friedman, O. M., et al., J. Amer. Chem. Soc., 81:3750 (1959), Bergel, F., et al., J. Chem. Soc., 1954, 2409, and Larionov, L. F., et al., Lancet, 269:169 (1955); 5-diazoimidazole-4-carboxamide described at Shealy, Y. F., et al., Biochem. Pharmacol., 11:674 (1962); nitrogen mustard described at Ross, W. C. J., et al., J. Chem. Soc., 1956, 1364, Ross, W. C. J., "Biological Alkylating Agents", Butterworth, London, England, 1962, and Bukhari, A., et al., J. Nat. Cancer Inst., 50:243 (1973); and dichlorodiamine, dichlorodialkylamine described at Rosenberg, B., Naturwissenshaften 60:399 (1973) and Cleare, M. J., Chem. Ind. (London), 1973, 921. Also, pivampicillin described by German Offenlegungsschrift No. 2,256,538; tetracycline described by French Patent No. 2,256,538; propoxyphene described by Gruber, C. M., Jr, et al., Toxicol. Appl. Pharmacol. 19:423 (1971) and U.S. Pat. No. 3,728,379; oleandomycin described by Canadian Patent No. 779,315; chloramphenicol described by Glazko, A. J., et al., Antibiot, Chemother., 2:234 (1952), German Offenlegungsschrift No. 2,244,197, Taylor, E. P., J. Pharm. Pharmacol., 5:254 (1953), and U.S. Pat. No. 3,442,926; lincomycin described by Sinkula, A. A., et al., J. Pharm. Sci., 58:1389 (1969), Sinkula, A. A., et al., ibid., 62.1757 (1973), Morozowich, W., et al., ibid., 62:1102 (1973) and Morozowich, W., et al., ibid., 58.1485 (1969); clindamycin described by Sinkula, A. A., et al., J. Pharm. Sci., 62.1106 (1973); erythromycin described by Stephen, V. C., et al., J. Amer. Pharm. Ass., Sci. Ed., 48:620 (1959), Sinkula, A. A., J. Pharm. Sci., 63:842 (1974), Clark, R. K., Jr., et al., Antibiot. Chemother., 7:487 (1957), and U.S. Pat. No. 2,967,129; ethyl mercaptan described by Davies, G. E., et al., Brit.

J. Pharmacol., 12:434 (1957), and Davies, G. E., et al., Nature, 182:664 (1958); trichloroethanol described by Caldwell, H. C., et al., J. Pharm. Sci., 56:920 (1967); and N-arylanthranilic acid described by U.S. Pat. No. 3,767,811. Also, chloramphenicol described at Glazko, A. J., et al., Antibiot. Annu., 1957–1958, 792, and Ross, S., et al., Antibiot. Annu., 1957–1958, 803; oleandomycin described by Canadian Patnet No. 779,315; and clindamycin described by Novak, E., et al., Int. J. Clin. Pharmacol. Ther. Toxicol., 3:201 (1970), Morozowich, W., et al., "Abstracts of Papers", APhA Academy of Pharmaceutical Sciences, Washington, D.C., meeting, April, 1970, p. 63, and Edmondson, H. T., Ann. Surg., 178:637 (1973).

While the naturally-occurring prostaglandins are carboxylic acids, numerous derivatives thereof are known in the art. For example, ester derivatives, including especially aromatic and phenacyl esters, are known in the art. See U.S. Pat. Nos. 3,069,332, 3,598,858, 3,979,440, and 3,984,062. Likewise, salts of these carboxylic acids are known in the art. See U.S. Pat. Nos. 3,069,332 and 3,958,858, cited above. Other derivatives of the prostaglandins, such as the amides thereof are known in the art. See U.S. Pat. Nos. 3,853,941, 3,884,942, 3,903299, 3,880,883, and 3,953,470. Further there are also known macrocyclic lactone derivatives of the prostaglandins as is, for example, described by E. J. Corey, et al., JACS 97:653 (1975) and U.S. Pat. Nos. 3,931,206, 4,067,991, 4,049,648, 4,032,543, 4,045,449, and 4,049,678.

SUMMARY OF THE INVENTION

The present invention provides bioprecursors for certain novel prostaglandin analogs.

The present invention further provides methods for the use of such bioprecursors.

In particular the present invention provides bioprecursors for a novel prostaglandin analog of the formula

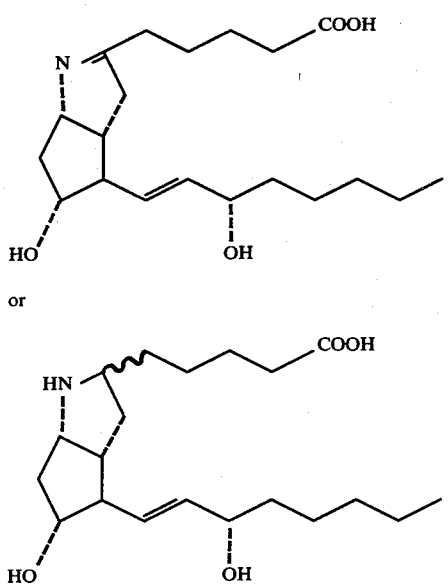

The present invention further provides a method of inducing in an animal a desirable pharmacological effect of a prostaglandin analog of the formula

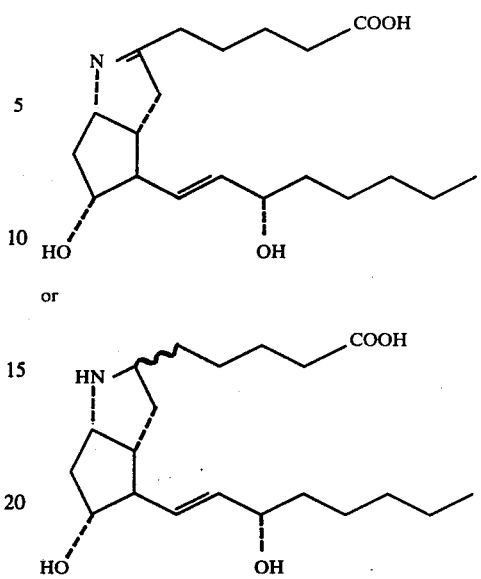

which comprises:

administering to said animal a dose of a bioprecursor of said prostaglandin analog effective to induce said desirable pharmacological effect by the hydrolysis in vivo of said bioprecursor to said prostaglandin analog.

These bioprecursors are useful for the same pharmacological purposes as the corresponding prostaglandin analogs, being hydrolyzable thereto in vivo.

The bioprecursors of the present invention are all useful for the same pharmacological purposes as the corresponding prostaglandin analogs from which they are prepared. While these bioprecursors have the same pharmacological effects, they are in many cases preferred over the corresponding prostaglandin analog by virtue of distinctive physical properties or distinctive pharmacological attributes.

For example, the selection of an appropriate bioprecursor can advantageously effect lipophilicity, as compared to the prostaglandin analog, and thereby advantageously modify the rate or manner of absorption.

Further, the bioprecursor may be preferentially distributed to a specific organ or tissue where its pharmacological effects will be exerted by hydrolysis at said tissue or organ.

Further, the pharmaceutical elegance of a particular prostaglandin analog can be advantageously affected by the selection of an appropriate bioprecursor, by modifying its sensory properties or its localized untoward effects at the site of administration. Further, the untoward GI effects of the prostaglandin analog can be advantageously modified by the selection of the appropriate bioprecursor. For example, the incidence or intensity of diarrhea may be reduced.

Moreover, the rate of hydrolysis of the bioprecursor to the prostaglandin analog will determine the dosage of prostaglandin analog in vivo. Accordingly the rate of hydrolysis in vivo is determined by conventional means, as indicated previously or known in the art, and used to determine the dose of the bioprecursor necessary to yield the desired endogenous release of the prostaglandin analog. Thus, as the various bioprecursors are hydrolyzed at varying rates, the release of prostaglandin analog in vivo will be more or less prolonged. Accordingly, when bioprecursors exhibiting relatively low rates of hydrolysis are employed, the pharmacological effects of bioprecursor administration are prolonged with the prolongation of release in vivo of the prostaglandin analog.

Furthermore, those bioprecursors which demonstrate no improvement in accordance with any of the desirable modifications described above, are nonetheless highly useful compositions of matter, in that such bioprecursors represent useful alternatives to the employment of the pharmacological agent itself.

The preparation of derivatives of the novel prostaglandin analogs from which bioprecursors are selected is accomplished by methods known in the art. See for example the references described above, and particularly Sinkula, A. A., et al., J. Pharm. Sci. 64:3259 (1975), and references cited therein.

Thereafter the selection of the derivatives of the prostaglandin analogs which represent bioprecursors thereof is likewise accomplished by means known in the art. See again the various references described above, as well as the description of the chemical, biochemical, and biological means for assessing the in vivo hydrolysis of the particular derivative.

Thereafter, the bioprecursor is employed for the same pharmacological purposes as are indicated for the prostaglandin analog itself. As indicated above, the rate of hydrolysis in vivo of the bioprecursor is employed in determing the dosage of the bioprecursor, from the known dosage of the prostaglandin analog itself. Likewise, having determined the modification in absorption characteristics or pharmaceutical elegance and acceptability which have been achieved by the bioprecursor, the bioprecursor is then employed either in the same manner as the prostaglandin analog itself, or in a manner whereby the modified properties of the bioprecursor require or permit a modification in the manner of use. Thus, for example, where the bioprecursor provides a more rapid and complete intestinal absorption, the bioprecursor is employed orally, but at a reduced dosage as compared to the prostaglandin analog itself.

As a further example, where the bioprecursor is slowly hydrolyzed to the prostaglandin analog, a larger dosage of the bioprecursor is given at the initiation of treatment, with a prolongation of pharmacological effect of the prostaglandin analog permitting fewer and less frequent subsequent administrations.

I claim:

1. A bioprecursor of a prostaglandin analog of the formula

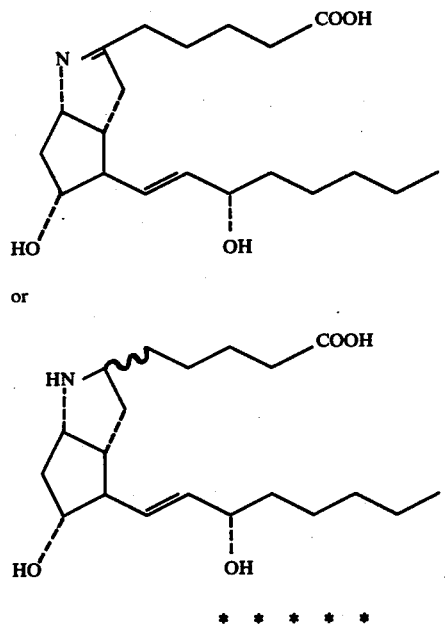

or

* * * * *

UNITED STATES PATENT OFFICE
CERTIFICATE OF CORRECTION

Patent No. 4,151,176      Dated April 24, 1979

Inventor(s) Gordon L. Bundy

It is certified that error appears in the above-identified patent and that said Letters Patent are hereby corrected as shown below:

In the Abstract, that portion of the formula reading

HO should read

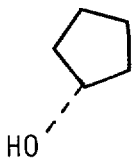

HO

Signed and Sealed this

Eleventh Day of September 1979

[SEAL]

Attest:

LUTRELLE F. PARKER

Attesting Officer    Acting Commissioner of Patents and Trademarks